United States Patent
Stetter et al.

(10) Patent No.: US 10,966,631 B2
(45) Date of Patent: Apr. 6, 2021

(54) BREATH SAMPLING DEVICES AND METHODS OF BREATH SAMPLING USING SENSORS

(71) Applicant: SPEC Sensors, LLC, Newark, CA (US)

(72) Inventors: Joseph R. Stetter, Hayward, CA (US); Vinay Patel, Fremont, CA (US); Melvin Findlay, Buchanan, GA (US)

(73) Assignee: Sensirion AG, Staefa Zh (CH)

( * ) Notice: Subject to any disclaimer, the term of this patent is extended or adjusted under 35 U.S.C. 154(b) by 272 days.

(21) Appl. No.: 14/851,417

(22) Filed: Sep. 11, 2015

(65) Prior Publication Data

US 2016/0073930 A1 Mar. 17, 2016

Related U.S. Application Data

(60) Provisional application No. 62/049,757, filed on Sep. 12, 2014.

(51) Int. Cl.
*A61B 5/08* (2006.01)
*A61B 5/097* (2006.01)
*G01N 33/497* (2006.01)

(52) U.S. Cl.
CPC .............. *A61B 5/082* (2013.01); *A61B 5/097* (2013.01); *A61B 2562/166* (2013.01); *G01N 33/497* (2013.01)

(58) Field of Classification Search
CPC ... A61B 5/082; A61B 5/097; A61B 2562/166; G01N 33/497
See application file for complete search history.

(56) References Cited

U.S. PATENT DOCUMENTS

| | | | |
|---|---|---|---|
| 4,924,860 A | 5/1990 | Larsen et al. | |
| 4,945,918 A | 8/1990 | Abernathy | |
| 4,948,679 A * | 8/1990 | Hunt | H01G 9/21 429/11 |
| 5,064,516 A | 11/1991 | Rupich | |

(Continued)

FOREIGN PATENT DOCUMENTS

| | | |
|---|---|---|
| CA | 2270809 | 10/1999 |
| CA | 2270809 A1 | 10/1999 |

(Continued)

OTHER PUBLICATIONS

Wang, J., "Decentralized Electrochemical Monitoring of Trace Metals: From Disposable Strips to Remote Electrodes," Analyst 119:763-766 (1994).

(Continued)

*Primary Examiner* — Navin Natnithithadha
*Assistant Examiner* — Andrey Shostak
(74) *Attorney, Agent, or Firm* — Dinsmore & Shohl LLP

(57) ABSTRACT

A breath sampling device including a housing having a fluid inlet positioned at a fluid inlet end, a fluid outlet positioned at a fluid outlet end, a fluid channel extending between the fluid inlet and the fluid outlet, and a sensor fluidly coupled to the fluid channel. The sensor is structurally configured to detect a presence of a target gas in a gas sample and a filter assembly fluidly coupled to the fluid channel and positioned between the fluid inlet and the sensor. The filter assembly is structurally configured to absorb heat, water vapor, or a combination thereof.

14 Claims, 6 Drawing Sheets

(56) References Cited

U.S. PATENT DOCUMENTS

| | | | |
|---|---|---|---|
| 5,173,166 A | 12/1992 | Tomantschger et al. | |
| 5,233,996 A | 8/1993 | Coleman et al. | |
| 5,239,492 A | 8/1993 | Hartwig | |
| 5,288,389 A | 2/1994 | Yamada et al. | |
| 5,429,105 A | 7/1995 | Bennett et al. | |
| 5,438,876 A | 8/1995 | Lewis | |
| 5,595,646 A | 1/1997 | Foos et al. | |
| 5,670,949 A | 9/1997 | Kirby et al. | |
| 5,876,577 A | 3/1999 | McAleer et al. | |
| 5,945,069 A | 8/1999 | Buehler | |
| 6,099,708 A | 8/2000 | Mallory et al. | |
| 6,158,431 A | 12/2000 | Poole | |
| 6,234,006 B1 | 5/2001 | Sunshine et al. | |
| 6,254,794 B1 | 7/2001 | Yokota et al. | |
| 6,454,923 B1 | 9/2002 | Dodgson et al. | |
| 6,513,362 B1 | 2/2003 | Yadav et al. | |
| 6,590,207 B2 | 7/2003 | Berger et al. | |
| 6,645,361 B1 | 11/2003 | Bloemer et al. | |
| 6,713,389 B2 | 3/2004 | Speakman | |
| 6,936,147 B2 | 8/2005 | Prohaska et al. | |
| 6,940,287 B2 | 9/2005 | Weyl et al. | |
| 7,077,938 B1* | 7/2006 | Austen | G01N 27/4045 204/431 |
| 7,189,341 B2 | 3/2007 | Li et al. | |
| 7,279,080 B2 | 10/2007 | Chapples et al. | |
| 7,422,646 B2 | 9/2008 | Prohaska et al. | |
| 7,445,941 B2 | 11/2008 | Buechler | |
| 8,152,991 B2 | 4/2012 | Briman et al. | |
| 8,747,635 B2 | 6/2014 | Murakami et al. | |
| 2002/0121438 A1* | 9/2002 | Saffell | G01N 27/404 204/415 |
| 2002/0166769 A1 | 11/2002 | Serikov | |
| 2003/0208133 A1 | 11/2003 | Mault | |
| 2004/0135684 A1 | 7/2004 | Steinthal et al. | |
| 2004/0135864 A1 | 7/2004 | Steinthal et al. | |
| 2004/0213702 A1 | 10/2004 | Ingrisch | |
| 2005/0083527 A1* | 4/2005 | Flaherty | A61B 5/097 356/437 |
| 2005/0274615 A1 | 12/2005 | Naito et al. | |
| 2006/0096871 A1 | 5/2006 | Manoukian et al. | |
| 2006/0191318 A1 | 8/2006 | McBride et al. | |
| 2007/0102294 A1 | 5/2007 | Dorisio Deininger et al. | |
| 2007/0144812 A1 | 6/2007 | Stewart et al. | |
| 2007/0154748 A1 | 7/2007 | Okuyama et al. | |
| 2008/0190174 A1 | 8/2008 | Kooi et al. | |
| 2008/0202930 A1 | 8/2008 | Mett | |
| 2008/0289962 A1 | 11/2008 | Prohaska et al. | |
| 2009/0040044 A1 | 2/2009 | Chiao | |
| 2009/0162750 A1 | 6/2009 | Kawakami et al. | |
| 2010/0057401 A1 | 3/2010 | Scheffler et al. | |
| 2010/0226824 A1 | 9/2010 | Ophir et al. | |
| 2011/0208081 A1* | 8/2011 | Smith | G01N 33/497 600/532 |
| 2011/0226041 A1 | 9/2011 | Cummins | |
| 2011/0246090 A1 | 10/2011 | Goya | |
| 2011/0288430 A1 | 11/2011 | Varney et al. | |
| 2012/0006096 A1 | 1/2012 | Ackley et al. | |
| 2012/0125772 A1 | 5/2012 | Stetter et al. | |
| 2012/0140431 A1 | 6/2012 | Faxvog et al. | |
| 2013/0126352 A1* | 5/2013 | Sekiya | G01N 27/4077 204/429 |
| 2013/0211207 A1* | 8/2013 | Joseph | A61M 16/104 600/301 |
| 2013/0265140 A1 | 10/2013 | Gudan et al. | |
| 2014/0018691 A1 | 1/2014 | McNeill | |
| 2014/0029085 A1 | 1/2014 | Bond et al. | |
| 2014/0174154 A1 | 6/2014 | Marra et al. | |
| 2014/0208829 A1 | 7/2014 | Lechner et al. | |
| 2014/0257127 A1 | 9/2014 | Smith et al. | |
| 2014/0311905 A1 | 10/2014 | Stetter et al. | |
| 2015/0160190 A1* | 6/2015 | Ravishankar | G01N 33/4972 73/1.06 |
| 2015/0250408 A1* | 9/2015 | Ssenyange | A61B 5/097 600/532 |
| 2016/0120458 A1* | 5/2016 | Yamada | A61B 5/441 600/306 |
| 2017/0226557 A1* | 8/2017 | Wang | C12Q 1/005 |

FOREIGN PATENT DOCUMENTS

| | | |
|---|---|---|
| DE | 2936142 | 3/1981 |
| DE | 3809107 | 9/1989 |
| DE | 19832395 | 11/1999 |
| GB | 2440556 | 2/2008 |
| GB | 2440556 A | 2/2008 |
| JP | 05-099886 | 4/1993 |
| JP | 08-327591 | 12/1996 |
| WO | 1990012315 | 10/1990 |
| WO | WO96/14576 | 5/1996 |
| WO | WO98/25138 | 6/1998 |
| WO | WO01/14864 | 3/2001 |
| WO | 20050114162 | 12/2005 |
| WO | 2013123500 | 8/2013 |
| WO | 2013123500 A1 | 8/2013 |
| WO | 2014143049 | 9/2014 |
| WO | 2014143049 A1 | 9/2014 |

OTHER PUBLICATIONS

Stetter, J.R., "Instrumentation to Monitor Chemical Exposure in the Synfuel Industry," Annals American Conf. of Governmental and Industrial Hygienists, 11:225-269 (1984).

Korotcenkov et al, "Review of Electrochemical Hydrogen Sensors," Chemical Reviews 109(3):1402-1433 (2009).

Stetter, J.R. et al, "Amperometric Gas Sensors—A Review," Modern Topics in Chemical Sensing: Chapter 4, Chemical Reviews, 108 (2):352-366 (2008).

Chang, S.C., et al, "Amperometric Gas Sensors", Talanta, 40(4):461-467 (1993).

International Search Report and Written Opinion issued in corresponding PCT International Application No. PCT/US2011/059075, dated Jan. 24, 2012.

International Search Report and Written Opinion issued in corresponding PCT International Application No. PCT/US2015/037893, dated Oct. 2, 2015.

International Search Report and Written Opinion issued in corresponding PCT International Application No. PCT/US2015/049631, dated Dec. 14, 2015.

International Search Report and Written Opinion issued in corresponding PCT International Application No. PCT/US2015/068251, dated Mar. 11, 2016.

International Search Report and Written Opinion issued in corresponding PCT International Application No. PCT/US2016/034314, dated Sep. 2, 2016.

International Search Report and Written Opinion issued in corresponding PCT International Application No. PCT/US2015/046053, dated Oct. 28, 2015.

Search Report for Application No. PCT/US15/49631 dated Dec. 14, 2015.

Search Report for Application No. PCT/US2015/068251 dated Mar. 11, 2016.

\* cited by examiner

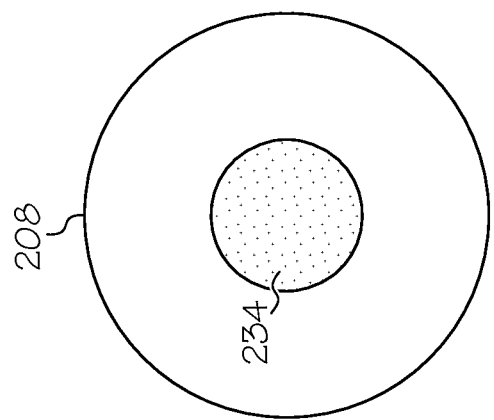
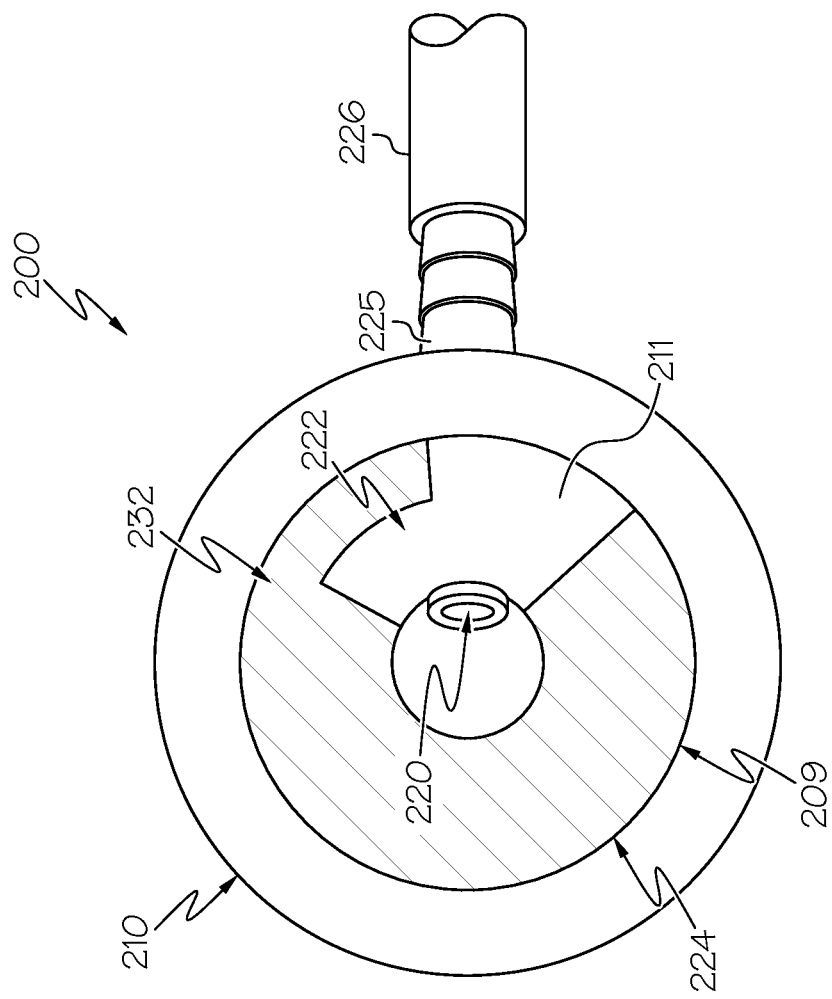
FIG. 4B
FIG. 4A

BREATH SAMPLING DEVICES AND METHODS OF BREATH SAMPLING USING SENSORS

CROSS-REFERENCE TO RELATED APPLICATIONS

This application claims the benefit of U.S. Provisional Application Ser. No. 62/049,757, filed Sep. 12, 2014.

TECHNICAL FIELD

The present specification generally relates to a breath sampling device interfaced with one or more sensors, for example, microelectronic gas sensors, printed gas sensors, or the like.

BACKGROUND

Sensors including electrochemical cells are used for detection of certain gases, for example, toxic gases and gases in a person's breath. In some sensors, high temperatures and high relative humidity may reduce the accuracy of sensor measurements.

Accordingly, breath sampling devices are desired that mitigate the effects of temperature and relative humidity of a gas sample before the gas sample enters a sensor configured to measure the gas sample.

SUMMARY

In one embodiment, a breath sampling device including a housing having a fluid inlet positioned at a fluid inlet end, a fluid outlet positioned at a fluid outlet end, a fluid channel extending between the fluid inlet and the fluid outlet, and a sensor fluidly coupled to the fluid channel. The sensor is structurally configured to detect a presence of a target gas in a gas sample and a filter assembly fluidly coupled to the fluid channel and positioned between the fluid inlet and the sensor. The filter assembly is structurally configured to absorb heat, water vapor, or a combination thereof.

In another embodiment, a breath sampling device including a housing having a fluid inlet positioned at a fluid inlet end, a fluid outlet positioned at a fluid outlet end, a fluid channel extending between the fluid inlet and the fluid outlet, and a printed gas sensor fluidly coupled to the fluid channel. The printed gas sensor is structurally configured to detect a presence of a target gas in a gas sample. The breath sampling device includes a humidity shield fluidly coupled to the fluid channel and positioned in a fluid flow path upstream the printed gas sensor and, upon contact between a gas sample and the humidity shield, the humidity shield absorbs water vapor present in the gas sample.

In another embodiment, a breath sampling device including a housing having a fluid inlet positioned at a fluid inlet end, a fluid outlet positioned at a fluid outlet end, a fluid channel extending between the fluid inlet and the fluid outlet, and a printed gas sensor fluidly coupled to the fluid channel. The printed gas sensor is structurally configured to detect a presence of a target gas in a gas sample. The breath sampling device includes a heat dissipation shield fluidly coupled to the fluid channel and positioned in the fluid flow path upstream the printed gas sensor and, upon contact between a gas sample and the heat dissipation shield, the heat dissipation shield absorbs heat present in the gas sample.

In another embodiment, a breath sampling device including a housing having a fluid inlet positioned at a fluid inlet end, a fluid outlet positioned at a fluid outlet end, a fluid channel extending between the fluid inlet and the fluid outlet, and a printed gas sensor fluidly coupled to the fluid channel. The printed gas sensor is structurally configured to detect a presence of a target gas in a gas sample. The breath sampling device includes a humidity shield fluidly coupled to the fluid channel and positioned in a fluid flow path upstream the printed gas sensor and, upon contact between a gas sample and the humidity shield, the humidity shield absorbs water vapor present in the gas sample. The breath sampling device further includes a heat dissipation shield fluidly coupled to the fluid channel and positioned in the fluid flow path upstream the printed gas sensor and, upon contact between a gas sample and the heat dissipation shield, the heat dissipation shield absorbs heat present in the gas sample.

In yet another embodiment, a breath sampling device includes a housing having a fluid inlet positioned at a fluid inlet end, a fluid outlet positioned at a fluid outlet end, and a fluid channel extending between the fluid inlet and the fluid outlet. The fluid channel is bounded by an inner surface of the housing. The breath sampling device includes a heat dissipation shield covering a portion of the inner surface of the housing and, upon contact between a gas sample and the heat dissipation shield, the heat dissipation shield absorbs heat present in the gas sample. The breath sampling device further includes a plug portion removably positionable in the fluid outlet, the plug portion comprising a humidity shield and, upon contact between a gas sample and the humidity shield, the humidity shield absorbs water vapor present in the gas sample.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 4A schematically depicts a housing with a thermally conductive coating as a portion of an example breath sampling device according to one or more embodiments shown or described herein;

FIG. 4B schematically depicts a plug portion of an example breath sampling device according to one or more embodiments shown or described herein;

DETAILED DESCRIPTION

Embodiments of the present disclosure are directed to a breath sampling device comprising a sensor configured to measuring the presence, amount, and/or concentration of a target gas in a gas sample and comprising a filter assembly configured to modify various properties of the gas sample before the gas sample enters the sensor. In some embodiments, the filter assembly includes a heat dissipation shield configured to absorb heat present within the gas sample before the gas sample enters the sensor. In some embodiments, the filter assembly also includes a humidity shield configured to absorb water vapor present within the gas sample before the gas sample enters the sensor. In operation, the heat dissipation shield slows the entrance of heat into the sensor and the humidity shield slows the entrance of water vapor into the sensor. Further, in operation, the filter assembly increases the accuracy and effectiveness of sensor measurements performed by the sensor by allowing the gas sample to enter the sensor with temporarily normalized (e.g., reduced) temperature and relative humidity.

Figure 1:
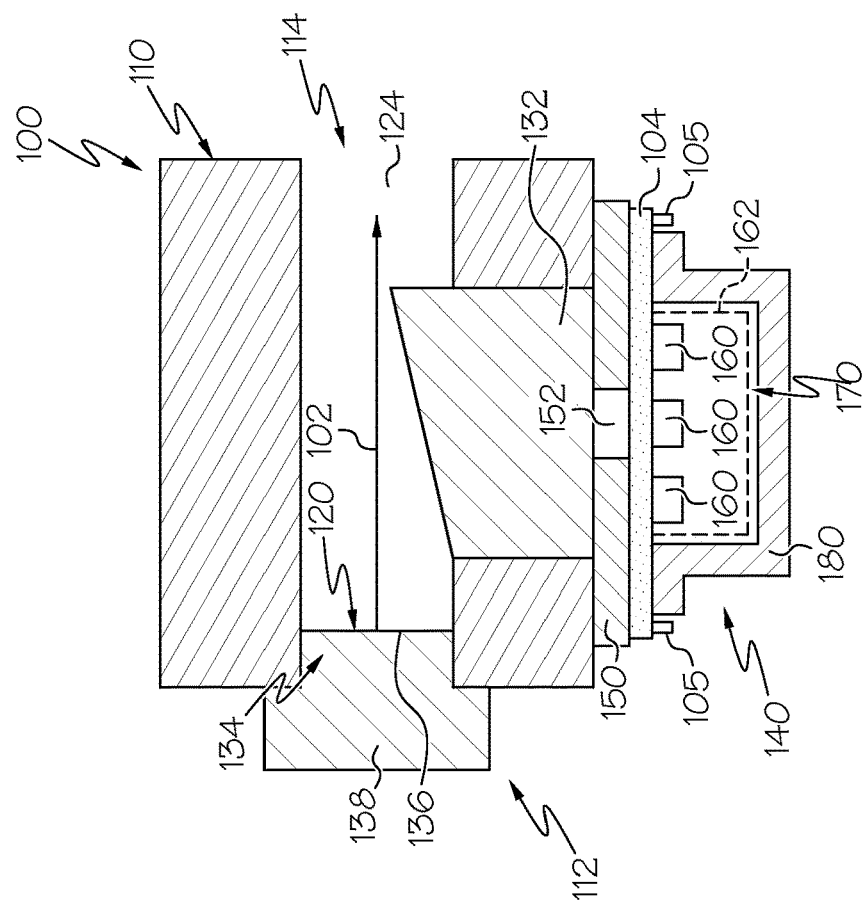
FIG. 1 schematically depicts an example breath sampling device according to one or more embodiments shown or described herein.
Figure 2:
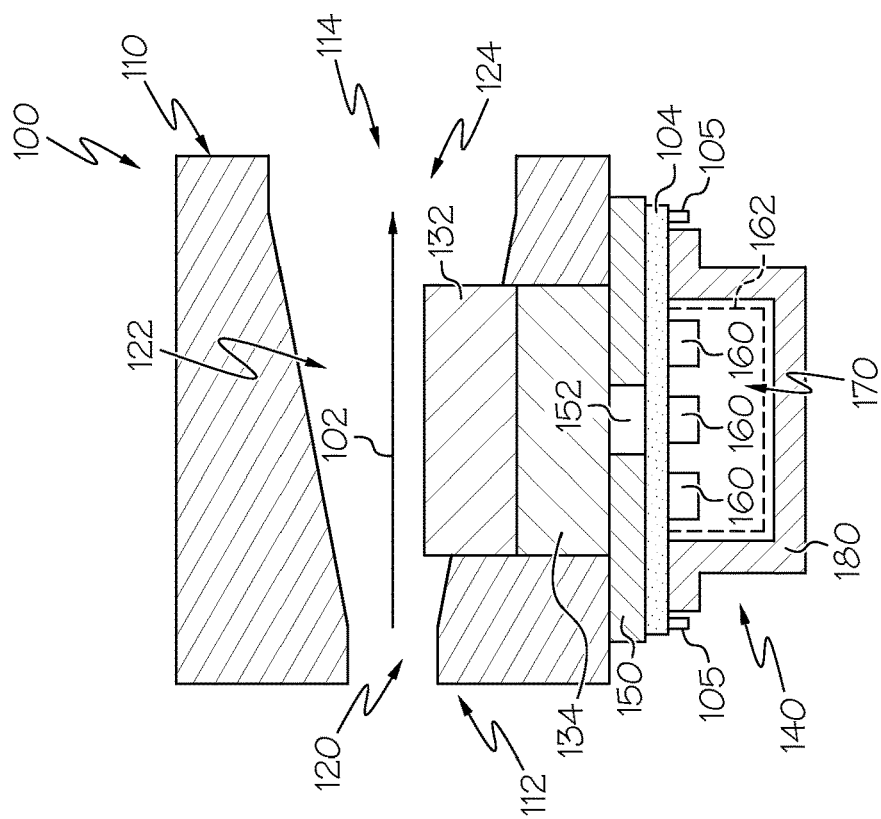
FIG. 2 schematically depicts another example breath sampling device according to one or more embodiments shown or described herein.

Referring now to FIGS. 1 and 2, the breath sampling device 100 is depicted. The breath sampling device 100 comprises a housing 110 having a fluid inlet 120 positioned at a fluid inlet end 112 of the housing 110 and a fluid outlet 124 positioned at a fluid outlet end 114 of the housing 110. The fluid inlet 120 and the fluid outlet 124 are fluidly, coupled by a fluid channel 122 that extends between the fluid inlet 120 and the fluid outlet 124. Further, a fluid flow path 102 extends along the fluid channel 122. In some embodiments, the fluid channel 122 may comprise a sulfonated tetra fluoroethylene based fluoropolymer-copolymer tube, such as a Nafion™ tube and the fluid inlet 120 and the fluid outlet 124 may be fluidly coupled by a Nation™ tube. In this embodiments, the fluid channel 122 may comprise a humidity shield 134, as described in more detail below. In some embodiments, the housing 110 comprises one or more chemically inert plastic materials, such as polytetrafluoroethylene (PTFE), polyimide, polycarbonate substrate, polyethylene terephthalate (PET) substrate, fluorinated ethylene propylene (FEP), polyether ether ketone (PEEK), acrylic, polypropylene (PP), or the like. The housing 110 may be any size, for example, between about 100 cm³ and about 1000 cm³, such as 250 cm³, 500 cm³, 750 cm³, or the like. Further, the housing 110 may be porous or partially porous (e.g., porous to some but not all gases). The size and porosity of the housing 110 may be configured to not impede the target gas of the gas sample.

In some embodiments, as depicted in FIG. 1, the housing 110 may have a smaller cross sectional area at the fluid inlet end 112 than at the fluid outlet end 114. For example, the fluid inlet 120 may have a smaller cross sectional area (e.g., a smaller diameter) than the fluid outlet 124. Further, the fluid channel 122 may comprise a tapered shape, increasing in cross sectional area from the fluid inlet end 112 to the fluid outlet end 114. In some embodiments, as depicted in FIG. 2, the fluid inlet 120 and the fluid outlet 124 may comprise uniform cross sectional areas. In other embodiments, the housing 110 may have a larger cross sectional area at the fluid inlet end 112 than at the fluid outlet end 114. It should be understood that any housing 110 shape is contemplated.

In some embodiments, the fluid inlet 120 is fully or partially restricted. For example, a portion of a filter assembly 130 (e.g., a humidity shield 134) may be positioned in the fluid inlet 120 to form an interface at the fluid inlet 120. By restricting flow at the fluid inlet 120, the flowrate of the gas sample entering the fluid channel may be altered, for example, slowed. Further, in some embodiments, the fluid outlet 124 may be partially or fully restricted such that gas sample introduced into the fluid channel 122 is directed into a sensor 140. In some embodiments, the housing 110 may have an adjustable design to accommodate variable gas samples and variable gas sample input times. For example, the housing 110 may comprise a larger volume and a larger throughput to facilitate larger gas samples. In some embodiments, the housing 110 may be sized and configured for a specific gas sample size and a specific gas sample input time.

Referring still to FIG. 1, the sensor 140 of the breath sampling device 100 is fluidly coupled to the fluid channel 122 such that when the gas sample is introduced into the fluid channel 122, at least a portion of the gas sample enters the sensor 140. As described in more detail below, the sensor 140 may comprise a printed gas sensor. The sensor 140 is configured to measure a presence of the target gas in the gas sample and in some embodiments the sensor 140 is configured to measure an amount and/or concentration of target gas in the gas sample. As an example and not a limitation, the target gas may comprise $H_2S$, Ketone, NO, CO, ethanol, $CH_4$, or the like. In some embodiments, the gas sample may be a user's breath and the sensor 140 may be configured to measure $H_2S$, Ketone, NO, CO, and/or ethanol in the user's breath. In other embodiments, the gas sample may comprise an environmental gas sample, such as, natural gas, mercaptan, or the like. In one example embodiment, the sensor 140 may be configured to measure a target gas comprising $H_2S$ in a gas sample comprising mercaptan and in another embodiment, the sensor 140 may be configured to measure a target gas comprising $CH_4$ in a gas sample comprising natural gas or other hydrocarbons in gas or oil products. In operation, the gas sample may be introduced into the breath sampling device 100 with range of flowrates and pressures.

Referring still to FIGS. 1 and 2, the filter assembly 130 is fluidly coupled to the sensor 140 such that a portion of the gas sample that enters the fluid channel 122 contacts and/or traverses the filter assembly 130 before entering the sensor 140. The filter assembly 130 may comprise a heat dissipation shield 132, a humidity shield 134, or a combination of both. The heat dissipation shield 132 and the humidity shield 134 may be positioned within the fluid flow path 102 between the fluid inlet 120 and the sensors 140, for example, within the fluid channel 122, coupled to the sensors 140, integrated into the sensors 140, positioned within the fluid inlet 120, and/or positioned within the fluid outlet 124. The heat dissipation shield 132 may be positioned upstream the humidity shield 134, such that the gas sample traverses the heat dissipation shield 132 before traversing the humidity shield 134, or downstream the humidity shield 134, such that the gas sample traverses the humidity shield 134 before traversing the heat dissipation shield 132. Further, both the heat dissipation shield 132 and the humidity shield 134 are positioned upstream the sensors 140.

In some embodiments, the humidity shield 134 comprises any device or material configured to temporarily reduce (e.g., buffer) the relative humidity of the gas sample by temporarily absorbing and retaining water vapor present in the gas sample. The humidity shield 134 may comprise sulfonated tetra fluoroethylene based fluoropolymer-copolymer, such as Nafion™, for example a Nafion™ coating or substrate, a Nafion™ treated porous media such as filter paper, porous polypyrrole (PRY), or the like. In some embodiments, the humidity shield 134 may comprise one or more of glycerol, glycerol sulfuric acid, polyvinyl alcohol (PVA), humectant, a room temperature ionic liquid (MIL), a porous wick material, or the like. Further, the humidity shield 134 may comprise a sampler, an interface, a coating, a gas chromatograph, or the like.

In operation, the humidity shield 134 may separate the target gas from water vapor present in the gas sample by receiving the gas sample and temporarily or permanently absorbing and retaining a portion of the water vapor present in the gas sample, for example, through relative capacitive migration. For example, the humidity shield 134 may be configured to retain an excess portion of the water vapor above a normalization level. The normalization level may comprise the relative humidity (e.g., water vapor) present in the humidity shield 134. If the relative humidity of the gas sample is higher than the normalization level, the humidity shield 134 will temporarily or permanently absorb the excess portion water vapor. For example, if the humidity shield 134 is designed with a normalization level of about 50% relative humidity, the humidity shield 134 will temporarily or permanently retain any excess water vapor above 50% relative humidity. Further, the humidity shield 134 may absorb and retain water vapor for a buffering period, for example, between about 5 and about 20 seconds, for example, 8 seconds, 10 second, 15 second, or the like. Further, in some embodiments, the humidity shield 134 may be configured to buffer the flowrate of the gas sample.

In some embodiments, as depicted in FIG. 2, the humidity shield 134 may be positioned at the fluid inlet 120, for example, the humidity shield 134 may be positioned in an inlet filter interface 136, for example, a coating or substrate comprising any of the components of the humidity shield 134 described above. The inlet filter interface 136 is porous and may fully or partially cover the fluid inlet 120. In some embodiments, the inlet filter interface 136 comprises a replaceable filter mouthpiece 138 that is removably engageable with to the fluid inlet 120. The humidity shield 134 (e.g., a Nafion™ coating, or the like) may be positioned within the replaceable filter mouthpiece 138 and in operation, the humidity shield 134 may be regenerated (e.g., automatic regeneration after a period of time) or replaced.

Referring again to FIGS. 1 and 2, the heat dissipation shield 132 comprises any device or material configured to temporarily reduce (e.g., buffer) the temperature of the gas sample by temporarily or permanently absorbing and retaining heat present in the gas sample, for example, through heat distribution and upon contact between the gas sample and the heat dissipation shield 132. The heat dissipation shield 132 may comprise thermally conductive metals and ceramics configured to remove heat from the gas sample without substantially reacting with or impeding the target gas. For example, the heat dissipation shield 132 may comprise a metal foil, such as aluminum foil, copper foil, a metalized polyester resin, such as a metalized MYLAR polyester resin, a thin metal coating, a porous metal screen, a TEE coated metal screen, any high thermal transfer media, or the like. Further, the heat dissipation shield 132 may comprise one or more of a sampler, an interface, a coating, a gas chromatograph, or the like. In some embodiments, the heat dissipation shield 132 may be configured to buffer the flowrate of the gas sample.

Figure 3B:
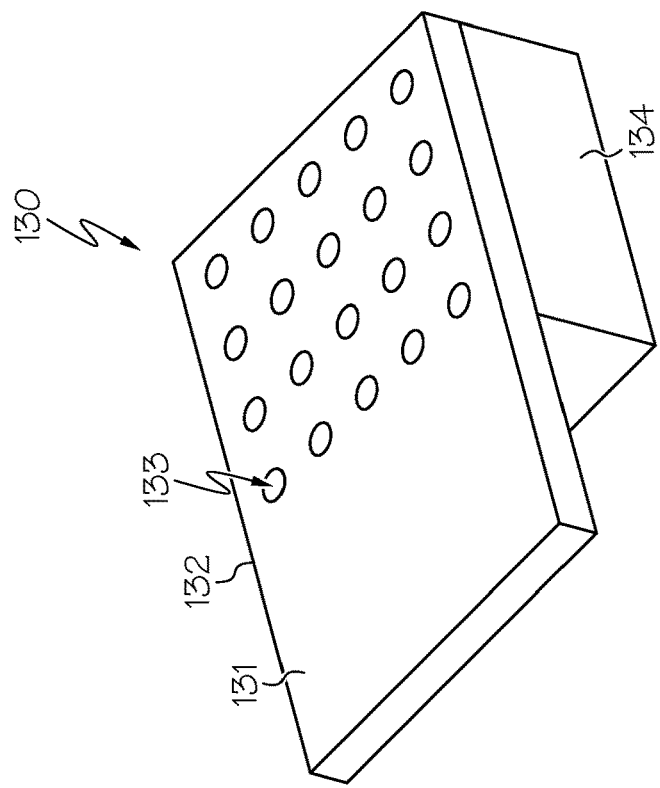
FIG. 3B schematically depicts an example filter assembly comprising a heat dissipation shield having an array of holes extending through of a portion of the heat dissipation shield according to one or more embodiments shown or described herein.
Figure 3A:
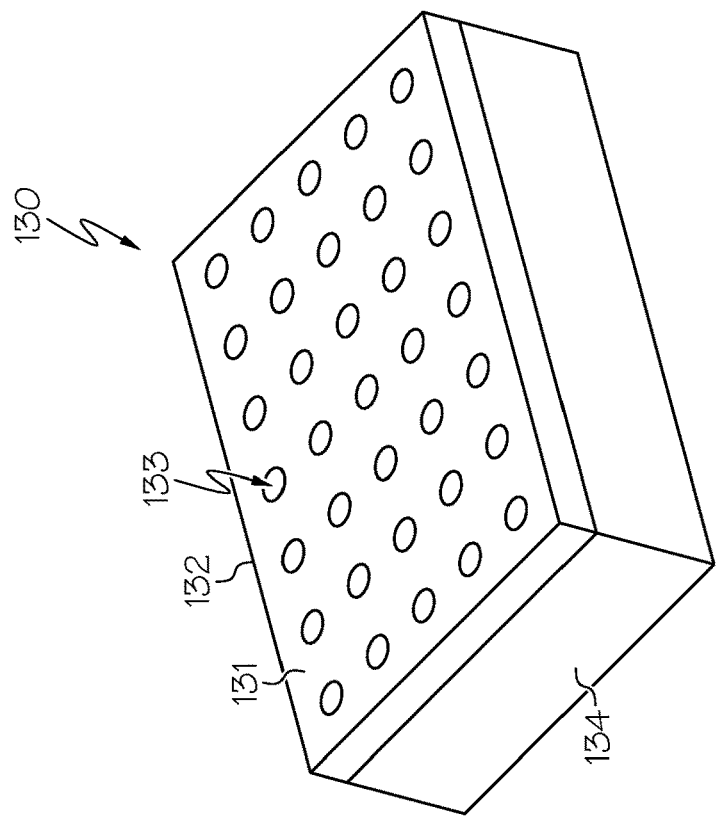
FIG. 3A schematically depicts an example filter assembly comprising a heat dissipation shield having an array of holes according to one or more embodiments shown or described herein.

Referring now to FIGS. 3A and 3B, the heat dissipation shield 132 may comprise a metal foil having an array of holes 133 disposed through a surface 131 of the heat dissipation shield 132. In some embodiments, the arrays of holes 133 are disposed through a portion of the surface 131 (FIG. 3B) and in other embodiments, the array of holes 133 are disposed though the entire surface 131 (FIG. 3A). In operation, the gas sample may travel over the surface 131, which removes heat from the gas sample and then pass through the array of holes 133. The longer the gas sample contacts the surface 131, the more heat may be removed from the gas sample. Further, smaller and/or fewer holes within the array of holes 133 may facilitate increased heat removal. The array of holes 133 may comprise uniform or non-uniform shapes and cross sectional areas (e.g., diameters in embodiments comprising round holes). For example, the array of holes 133 may comprise diameters of between about 0.1 mm and 10 mm, e.g., about 1 mm, 2 mm, 5 mm, or the like.

Referring again to FIGS. 1 and 2, the heat dissipation shield 132 may be a baffle comprising tubes, tube bundles, flow-directing vanes, obstructing vanes, panels, or a combination thereof. In some embodiments, the baffle may comprise a slot or a tube positioned within the fluid channel 122 and may comprise a length to diameter ratio of between about 3/1 and about 10/1, for example, 4/1, 6/1, 8/1, or the like. In some embodiments, as depicted in FIG. 2, the heat dissipation shield 132 may be aerodynamic (e.g., an aerodynamic baffle) such that the heat dissipation shield minimally intrudes the fluid flow path 102 of the fluid channel 122. In some embodiments, the aerodynamic heat dissipation shield 132 may be positioned in the fluid channel 122 when minimal gas sample flowrate alteration is desired. Further, the heat dissipation shield 132 may be porous or non-porous. When the heat dissipation shield 132 is non-porous, the gas sample may contact the heat dissipation shield 132 without passing through the heat dissipation shield 132. An example non-porous heat dissipation shield 132 is depicted in FIGS. 4A-5B, described in more detail below, in which the heat dissipation shield 132 comprises foil disposed on inner surface of the housing 110, such that the foil is positioned in the fluid channel 122.

In operation, the heat dissipation shield 132 may buffer and/or reduce the temperature in the gas sample, which may reduce the effects of temperature on the measurements performed by the sensor 140. For example, a gas sample comprising a temperature of about 40° C. can traverse the heat dissipation shield 132 and enter the one or more sensors 140 at a temperature between about 15° C. and about 30° C., such as about 20° C., 23° C., 26° C., or the like. In some embodiments, the heat dissipation shield 132 may absorb and retain heat for a buffering period, for example, between about 5 and about 20 seconds, for example, 8 seconds, 10 second, 15 second, or the like.

Referring to FIGS. 1, 3A, and 3B, the heat dissipation shield 132 may be coupled to or adjacent the humidity shield 134. For example, the heat dissipation shield 132 having the array of holes 133 may be positioned adjacent the humidity shield 134 such that the gas sample passes over the surface 131 of the heat dissipation shield 132 and through the array of holes 133 before or after entering the humidity shield 134.

After traversing the heat dissipation shield 132 and the humidity shield 134, the gas sample enters the sensor 140. In one example embodiment, the heat dissipation shield 132 comprises about 1-5 layers of aluminum foil (e.g., about 5-20 mils) and the humidity shield 134 comprises between about 100 and 250 µm of a porous material coated with Nafion™, for example, about 125 µm, 175 µm, and 225 µm, or the like. In some embodiments, the heat dissipation shield 132 and the humidity shield 134 are combined in a single material, for example, a composite material comprising a foil material coated or combined with Nafion™, or the like.

In operation, temperature or relative humidity present in the gas sample above or below a desired range may cause measurement errors in the sensor 140. Further, temperature or relative humidity may have an increased effect when the gas sample includes a small amount of the target gas, for example, when the target gas is present in part per million (ppm) or part per billion (ppb) levels, such as between about 1 ppb and about 300 ppb of the target gas. Further, in one example embodiment, a 38° C. gas sample having a relative humidity of 95% may enter the breath sampling device 100 and traverse the filter assembly 130 which lowers the temperature to about 22° C. and lowers the relative humidity to about 50%.

Figure 4C:
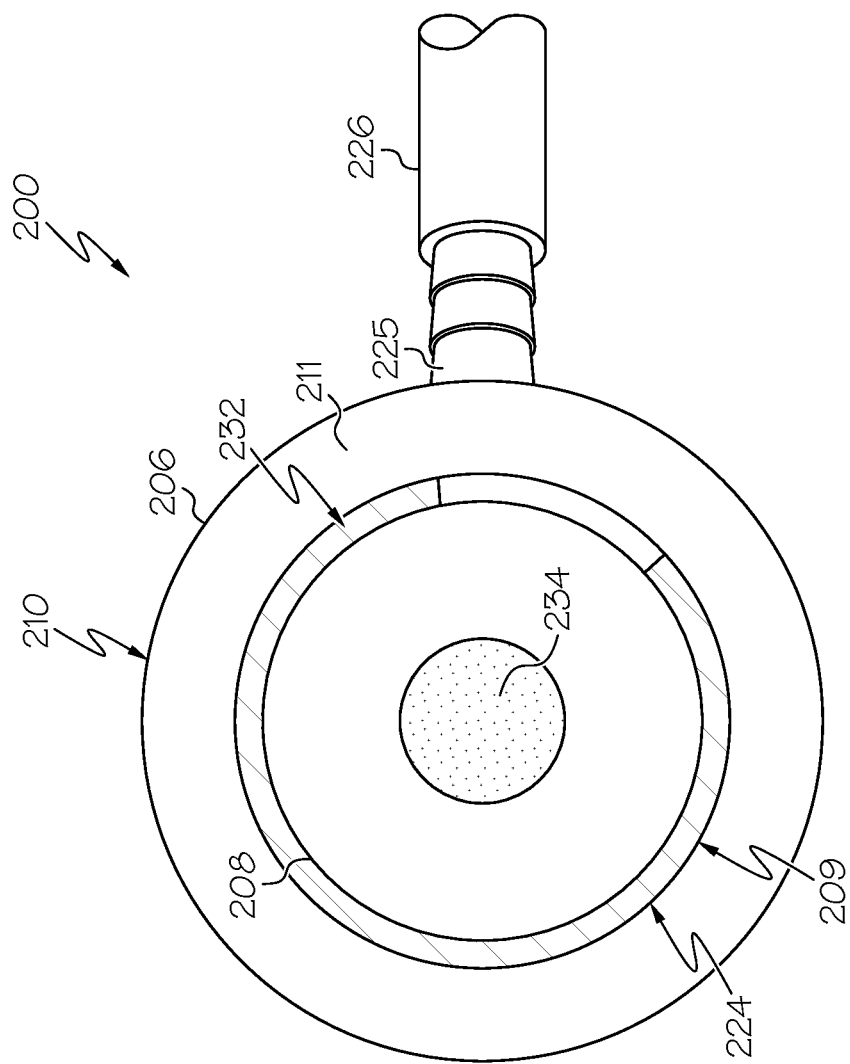
FIG. 4C schematically depicts the plug portion of FIG. 4B positioned within the thermally conductive housing of FIG. 4A according to one or more embodiments shown or described herein.

Referring now to FIGS. 4A-4C, another breath sampling device 200 is depicted. The breath sampling device 200 includes a housing 210 having a fluid inlet 220, a fluid outlet 224, and a fluid channel 222 extending therebetween. In some embodiments, a nozzle 225 may be positioned in the fluid inlet 220. The nozzle 225 may comprise any fluid nozzle configured to receive a gas sample. Further, a tube 226 may be coupled to the nozzle 225 such that a user may provide a gas sample through the tube 226. The housing 210 comprises an inner surface 211 facing the fluid channel 222 and a heat dissipation shield 232 that may be positioned in the housing 210, for example, partially or fully covering the inner surface 211. For example, the heat dissipation shield 232 may comprise a metal foil that covers the inner surface 211 of the housing 210.

Referring now to FIGS. 4B and 4C, the breath sampling device 200 may further comprise a plug portion 208 removably engageable with the housing 210, for example with a plug receiving portion 209 of the housing 210. In some embodiments, the plug receiving portion 209 is the fluid outlet 224 of the housing 210. In other embodiments, the plug receiving portion 209 and the fluid outlet 224 are positioned in different locations of the housing 210. In some embodiments, the plug portion 208 includes a humidity shield 234. The plug portion 208 and the humidity shield 234 can vary in size to control the amount of gas sample that enters the sensor 240, depicted in FIGS. 5A-5B, below.

Figure 5A:
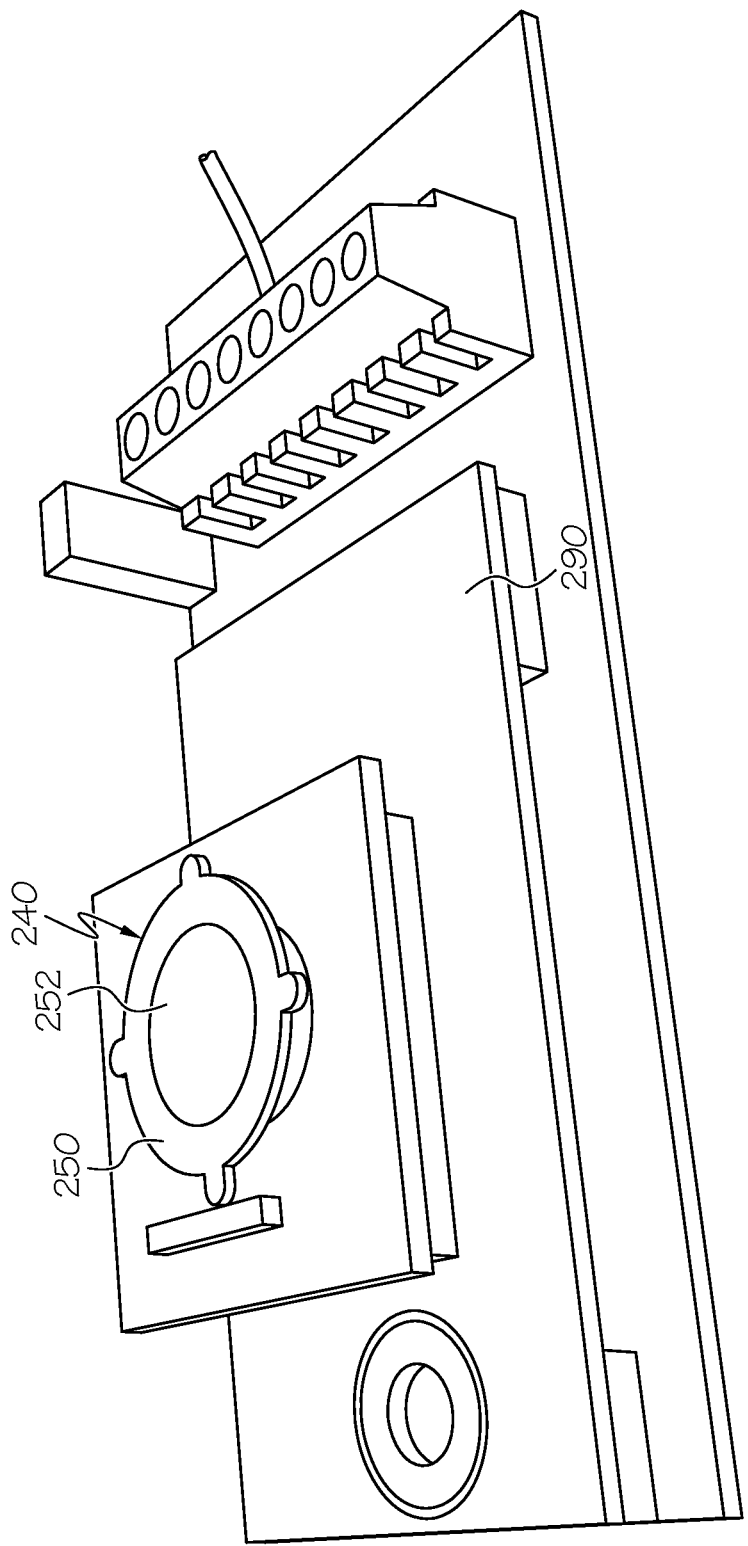
FIG. 5A schematically depicts a printed gas sensor of a breath sampling device according to one or more embodiments shown or described herein.
Figure 5B:
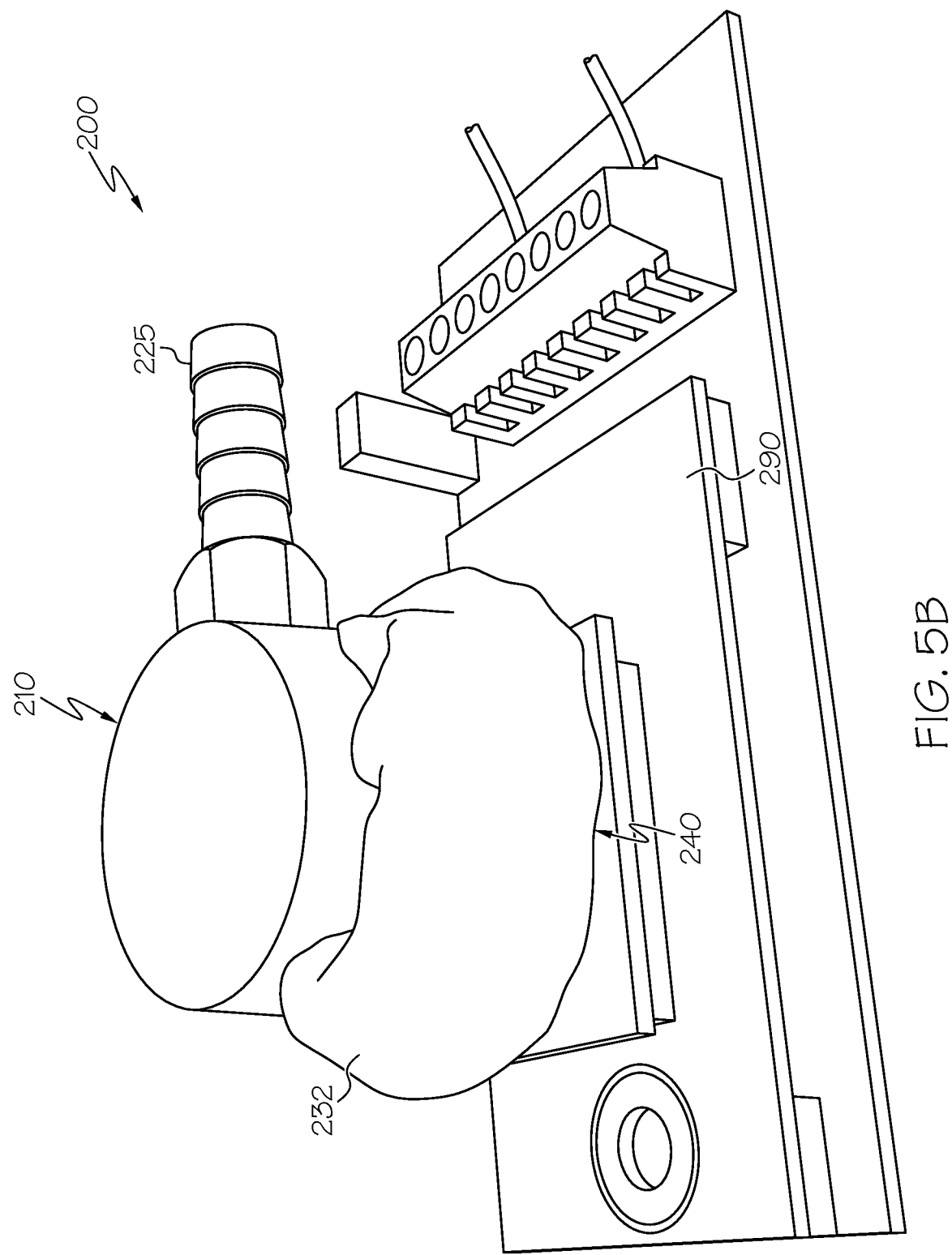
FIG. 5B schematically depicts the breath sampling device of FIGS. 4A and 4B coupled to the printed gas sensor of FIG. 5A according to one or more embodiments shown or described herein.

In operation, when the gas sample enters the housing 210, the heat dissipation shield 232 covering the inner surface 211 of the housing 210 absorbs heat in the gas sample upon contact between the gas sample and the heat dissipation shield 232. Next, the gas sample exits the housing 210 through the plug portion 208 comprising the humidity shield 234 which, upon contact between the gas sample and the humidity shield 134, absorbs water vapor from the gas sample before the gas sample enters the sensor 240. Referring now to FIGS. 5A and 5B, the sensor 240 may be positioned on a printed circuit board 290. Further, the sensor 240 is engageable with the housing 210, for example, the housing 210 is engageable with a gas inlet region 252 positioned in a substrate 250 of the sensor 240 such that the gas sample passes through the plug portion 208 before entering the sensor 240.

In operation, after the heat dissipation shield 132 and the humidity shield 134 may require some recovery time, (e.g., the time it takes for temperature and relative humidity to return to baseline levels after the gas sample has entered the breath sampling device 100). The recovery time may be correlated with the design of the breath sampling device 100, for example, an example breath sampling device 100 having a small housing 110 may require a shorter recovery time than an example breath sampling device 100 with a larger housing 110. Further, in some embodiments, the breath sampling device 100 may operate continuously without requiring recovery time. For example, the breath sampling device 100 may incorporate a compensation method, such as methods compensating for signal drift, known temperatures, and known relative humidities. In operation, the small components allow the breath sampling device 100 to reach steady state quickly, e.g., steady state within 10-20 seconds. Another example compensation method includes altering the signal speed by changing the thickness of the materials.

Referring again to FIGS. 1 and 2, the sensor 140 may comprise a printed gas sensor, a microelectromechanical gas sensor, or the like, for example the printed gas sensors disclosed in U.S. patent application Ser. No. 14/317,222 titled "Printed Gas Sensor," which is incorporated herein by reference. As an example and not a limitation, some embodiments of the sensor 140 are described below, although any exemplary sensor is contemplated. In some embodiments, the sensor 140 comprises a substrate layer 150 (e.g., a porous substrate or a partially porous substrate), one or more electrodes 160, an electrolyte cavity 170 or layer that houses liquid or gel electrolyte in electrolytic contact with the one or more electrodes 160, and an encapsulation layer 180. In some embodiments, the substrate layer 150 includes one or more gas access regions 152 fluidly coupled to the fluid channel 122 of the breath sampling device 100 to allow the gas sample to enter the sensor 140 and can be any shape and size. While one sensor 140 is depicted in FIGS. 1, 2, 5A, and 5B, it should be understood that any number of sensors 140 are contemplated.

The substrate layer 150 may comprise one or more partially porous substrates coupled together using pressure sensitive adhesive, or the like. The substrate layer 150 may comprise low temperature plastics such as polycarbonate substrate and PET, and/or high temperature material such as PTFE, porous PTFE, or polyimide. The encapsulation layer 180 may comprise a tetrafluoroethylene (TFE) substrate, or other plastic and can be utilized to block gas access. In some embodiments, the filter assembly 130 is positioned on the substrate layer 150 such that the gas sample must pass through the filter assembly 130 before traversing the one or more gas access regions 152 of the substrate layer 150.

The one or more electrodes 160 may be coupled to a wick 162 comprising porous glass fiber or glass fiber filter paper or may be coupled directly to the substrate layer 150. The one or more electrodes 160 may be screen printed, inkjet printed, stamped, or stenciled onto the wick 162 or substrate layer 150. The substrate layer 150 may further comprise a printed runner 104 facing the electrolyte cavity 170. The electrolyte cavity 170 may house an electrolyte, for example $H_2SO_4$. The one or more electrodes 160 may comprise PTFE liquid, PTFE powder, polypropylene powder or polyethylene powder, as well as catalyst, solvents, and additives, such as, for example, platinum, palladium, or alloys or supported catalysts like platinum on carbon. In some embodiments, multiple electrodes 160 may be configured to each detect different target gases. For example, a first electrode can detect CO and a second electrode can detect gases such as $H_2S$, $O_3$, $SO_4$, or $NO_2$. In some embodiments, the one or more electrodes 160 are curable at temperatures lower than the melting point and deformation point of the materials of the sensor 140.

In operation, the electrochemical reaction between the electrode 160, the electrolyte, and the target gas generates an electric current in the printed runner 104 and sends electric signal to one or more circuits connected to the printed runner 104 at one or more electrical contact points 105. This electric signal communicates to one or more circuits that a target gas is detected in the sensor 140. It should be understood that any sensor 140 configured to evaluate a gas sample may be included in the breath sampling device 100, 200 of the present disclosure, for example, any sensor 140 having temperature and relative humidity sensitivities. In some embodiments, sensors 140 having a pt/Ru catalyst may provide a fast response time and a high bias for large signals. Additionally, optimization of the target gas may be performed in the sensor 140. Some sensors 140 having electrolytes comprising RTIL may have lower relative humidity signals and lower temperature coefficients.

In one example, a dual sensor compensation method is contemplated allowing one or more sensors 140 to measure multiple target gases in the gas sample without a first target gas altering the measurement of a second target gas, and vice versa. In one example embodiment, two sensors 140 are contemplated, one configured to measure nitric oxide (NO) and another configured to measure $H_2S$. To compensate for NO interference, the breath sampling device 100 may include two sensors, a first sensor for NO detection having a $H_2S$ filter (e.g., bicarbonate) and a second sensor having a filter that responds to NO and $H_2S$. The difference in the sensor measurements allows for computation of both NO and $H_2S$ concentrations. For example, when the gas sample is a user's breath, NO on the breath may be an indicator of asthma and/or stress. In other embodiments, this dual sensor compensation method may be used to compensate for acetone, $CO_2$ or other example gas samples.

In some embodiments, the effects of temperature and relative humidity on the one or more sensors 140 may be minimized by an additional electrode, such as, for example, a compensation electrode. The compensation electrode may be configured as a working electrode communicatively coupled to a differential amplifier which generates a signal that can be subtracted from the primary signal measurements. The compensation electrode may compensate for the effects of temperature and relative humidity on the sensor measurement. In some embodiments, the compensation electrode may be buried under a gas impermeable layer of low thermal mass material, (i.e. Nafion™, or the like, as described above configured to absorb water vapor). Additionally, in some embodiments, a catalyst with a low surface area may be coupled to the one or more electrodes 160 to increase the signal to noise ratio of the one or more sensors 140 and reduce the magnitude of the baseline effects of temperature and relative humidities. This may allow use of higher gain to improve resolution of the sensor 140. In some embodiments, the method detection limit of the sensor 140 for the measurement of the target gas is between about 50 ppb and about 250 ppb of the target gas, e.g., about 100 ppb, 150 ppb, 200 ppb, or the like.

It should now be understood that breath sampling devices are contemplated that include a sensor configured to measuring the presence, amount, and/or concentration of a target gas in a gas sample and a filter assembly configured to modify various properties of the gas sample before the gas sample enters the sensor. The filter assembly includes a humidity shield and/or the heat dissipation shield. The heat dissipation shield is configured to absorb heat present within the gas sample before the gas sample enters the sensor and the humidity shield is configured to absorb water vapor present within the gas sample before the gas sample enters the sensor. In operation, the heat dissipation shield slows the entrance of heat into the sensor and the humidity shield slows the entrance of water vapor into the sensor. Reducing the temperature and the relative humidity of the gas sample that enters the sensor may increase the accuracy and effectiveness of sensor measurements.

It is noted that the term "substantially" may be utilized herein to represent the inherent degree of uncertainty that may be attributed to any quantitative comparison, value, measurement, or other representation. This term is also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A breath sampling device comprising:
   a housing having a fluid inlet positioned at a fluid inlet end, a fluid outlet positioned at a fluid outlet end, and a fluid channel extending between the fluid inlet and the fluid outlet;
   a sensor fluidly coupled to the fluid channel, wherein the sensor is structurally configured to detect a presence of a target gas in a gas sample; and
   a filter assembly fluidly coupled to the fluid channel and positioned between the fluid inlet and the sensor, wherein the filter assembly is structurally configured to reduce the heat of the gas sample and reduce the humidity of the gas sample and the filter assembly comprises a heat dissipation shield comprising a thermally conductive metal having an array of holes, wherein the heat dissipation shield is fluidly coupled to the fluid channel such that a portion of the gas sample introduced into the fluid channel passes through the array of holes and wherein the heat dissipation shield is positioned relative to the sensor such that the gas sample comprises a higher temperature when the gas sample contacts the filter assembly than when the gas sample contacts the sensor.

2. The breath sampling device of claim 1, wherein the filter assembly comprises a humidity shield structurally configured to reduce humidity of the gas sample upon contact between the gas sample and the humidity shield.

3. The breath sampling device of claim 2, wherein the humidity shield comprises a sulfonated tetra fluoroethylene based fluoropolymer-copolymer, porous polypyrrole, glycerol, room temperature ionic liquid, polyvinyl alcohol, humectant, or a combination thereof.

4. The breath sampling device of claim 2, wherein the humidity shield retains the humidity removed from the gas sample for a buffering period.

5. The breath sampling device of claim 1, wherein the housing comprises a chemically inert plastic.

6. The breath sampling device of claim 1, wherein the fluid inlet comprises a first cross sectional area and the fluid outlet comprises a second cross sectional area, wherein the first cross sectional area is smaller than the second cross sectional area.

7. The breath sampling device of claim 1, wherein the sensor is a printed gas sensor comprising:
a substrate layer comprising one or more gas access regions;
one or more printed runners coupled to the substrate layer, wherein the one or more printed runners are electrically conductive;
an encapsulation layer coupled to the substrate layer and defining an electrolyte cavity positioned within the encapsulation layer;
one or more electrodes positioned in electrical communication with the one or more printed runners such that the one or more printed runners can transport an electronic signal produced by an electrochemical reaction at the one or more electrodes; and
an electrolyte housed within the electrolyte cavity.

8. The breath sampling device of claim 1, wherein the heat dissipation shield is positioned relative to the sensor such that the gas sample comprises a higher temperature when the gas sample contacts the filter assembly than when the gas sample undergoes an electrochemical reaction within the sensor.

9. A breath sampling device comprising:
a housing having a fluid inlet positioned at a fluid inlet end, a fluid outlet positioned at a fluid outlet end, and a fluid channel extending between the fluid inlet and the fluid outlet;
a printed gas sensor fluidly coupled to the fluid channel, wherein the printed gas sensor is structurally configured to detect a presence of a target gas in a gas sample; and
a heat dissipation shield fluidly coupled to the fluid channel and positioned in a fluid flow path upstream of the printed gas sensor, wherein the heat dissipation shield comprises a thermally conductive metal having an array of holes, wherein the heat dissipation shield is fluidly coupled to the fluid channel such that a portion of the gas sample introduced into the fluid channel passes through the array of holes, and wherein, upon contact between the gas sample and the heat dissipation shield, the heat dissipation shield reduces the heat of the gas sample and the heat dissipation shield is positioned relative to the printed gas sensor such that the gas sample comprises a higher temperature when the gas sample contacts the heat dissipation shield than when the gas sample contacts the printed gas sensor.

10. The breath sampling device of claim 9, wherein the printed gas sensor is operable at a temperature between 15° C. and 30° C.

11. A breath sampling device comprising:
a housing having a fluid inlet positioned at a fluid inlet end, a fluid outlet positioned at a fluid outlet end, and a fluid channel extending between the fluid inlet and the fluid outlet;
a printed gas sensor fluidly coupled to the fluid channel, wherein the printed gas sensor is structurally configured to detect a presence of a target gas in a gas sample;
a humidity shield fluidly coupled to the fluid channel and positioned in a fluid flow path upstream of the printed gas sensor, wherein, upon contact between the gas sample and the humidity shield, the humidity shield reduces the humidity of the gas sample; and
a heat dissipation shield fluidly coupled to the fluid channel and positioned in the fluid flow path upstream of the printed gas sensor, wherein the heat dissipation shield comprises a thermally conductive metal having an array of holes, wherein the heat dissipation shield is fluidly coupled to the fluid channel such that a portion of the gas sample introduced into the fluid channel passes through the array of holes, and wherein, upon contact between the gas sample and the heat dissipation shield, the heat dissipation shield reduces the heat of the gas sample and the heat dissipation shield is positioned relative to the printed gas sensor such that the gas sample comprises a higher temperature when the gas sample contacts the heat dissipation shield than when the gas sample contacts the printed gas sensor.

12. The breath sampling device of claim 11, wherein the humidity shield comprises a sulfonated tetra fluoroethylene based fluoropolymer-copolymer, porous polypyrrole, glycerol, room temperature ionic liquid, polyvinyl alcohol, humectant, or a combination thereof.

13. The breath sampling device of claim 11, wherein the humidity shield retains the humidity removed from the gas sample for a buffering period.

14. The breath sampling device of claim 11, wherein the heat dissipation shield is positioned relative to the printed gas sensor such that the gas sample comprises a temperature of less than 40° C. when the gas sample undergoes an electrochemical reaction within the printed gas sensor.

* * * * *